United States Patent [19]

Caruccio et al.

[11] 4,328,001

[45] May 4, 1982

[54] METHOD OF DETERMINING WEATHERING CHARACTERISTICS OF ROCK FORMATIONS IN EARTH MOVING OPERATIONS

[76] Inventors: Frank T. Caruccio; Gwendelyn G. Caruccio, both of 3820 Edinburgh Rd., Columbia, S.C. 29204

[21] Appl. No.: 184,994

[22] Filed: Sep. 8, 1980

[51] Int. Cl.³ .............................................. G01N 33/24
[52] U.S. Cl. ............................... 23/230 EP; 23/230 R
[58] Field of Search ....................... 23/230 R, 230 EP; 364/497; 422/68; 299/1, 95

[56] References Cited

U.S. PATENT DOCUMENTS 3,605,501 9/1971 Chenevert ........................ 73/432 R

OTHER PUBLICATIONS

Standard Methods for the Examination of Water and Waste Water, 13th Edition, published by American Public Health Assoc., pp. 50–57.
Infanger et al., "Positioning Acid-Producing Overburden for Minimal Pollution," Presented at Symp. on Surface Mining Hydrology, Sedimentology and Reclamation at the Univ. of Kentucky, Lexington, Ky., Dec. 1–5, 1980.
Geidel et al., "Time as a Factor in Acid Mine Drainage Pollution," pp. 41–50 of Capers presented before Seventh Symposium of Coal Mine Drainage Research (Oct. 18–20, 1977).
Caruccio, The Ecology of Resource Degradation and Renewal, pp. 197–205, Blackwell Scientific Publications, 1975.
Geidel et al., "Geochem. Factors Affecting Coal Mine Drainage Quality," pp. 129–148 of Reclamation of Drastically Disturbed Lands, C. 1978, ASA-CSS-A-SSSA, Madison, Wisc.
"Field and Lab. Methods Applicable to Overburdens and Minesoils," U. S. Environ. Protection Agency, EPA-600/2-78-054, Mar. 1978.

*Primary Examiner*—Ronald Serwin

*Attorney, Agent, or Firm*—Luke J. Wilburn, Jr.; Wellington M. Manning, Jr.

[57] ABSTRACT

A method for producing graphic or mathematical boundary information, in the form of graphs and the like, and the use of such information, for more accurately predicting the acidity and alkalinity of water drainage from rock types which may be subjected to weathering conditions in earth moving operations.

Selected rock samples of particular rock types collected from a geographic location of interest are subjected to oxidation and leaching for a predetermined period of time to simulate natural weathering conditions to which the rock types may be exposed. The leachates from each rock sample are chemically analyzed by titration with standard acid and base solutions to selected end points to obtain their acidity or alkalinity concentrations, and these concentrations are differentiated for the particular rock sample to obtain a net acidity or alkalinity value for the rock sample.

Other portions of each rock sample are subjected to direct chemical analysis to determine their total acidity and alkalinity production potentials, and these total production potential values for a given rock type are plotted against each other on a suitable graph. Each sample plot is then identified as acidic or alkaline by its corresponding net acidity or alkalinity leachate value, and the so identified acid and alkaline plots are separated by a boundary line on the graph to establish areas of predicted acidity or alkalinity of the rock type to weathering conditions.

The boundary information as established on the graphs for each rock type is thereafter utilized by a field operator in an on-site location with total acid and alkaline production potential values obtained by direct chemical analysis of subsequent rock samples, to more accurately predict the acid or alkaline water drainage which will be produced from a rock sample when exposed to natural weathering conditions.

Such methods and data so produced are useful in mine permitting, and in mining operations to facilitate relocation of overburden materials to minimize acid water drainage therefrom.

15 Claims, 1 Drawing Figure

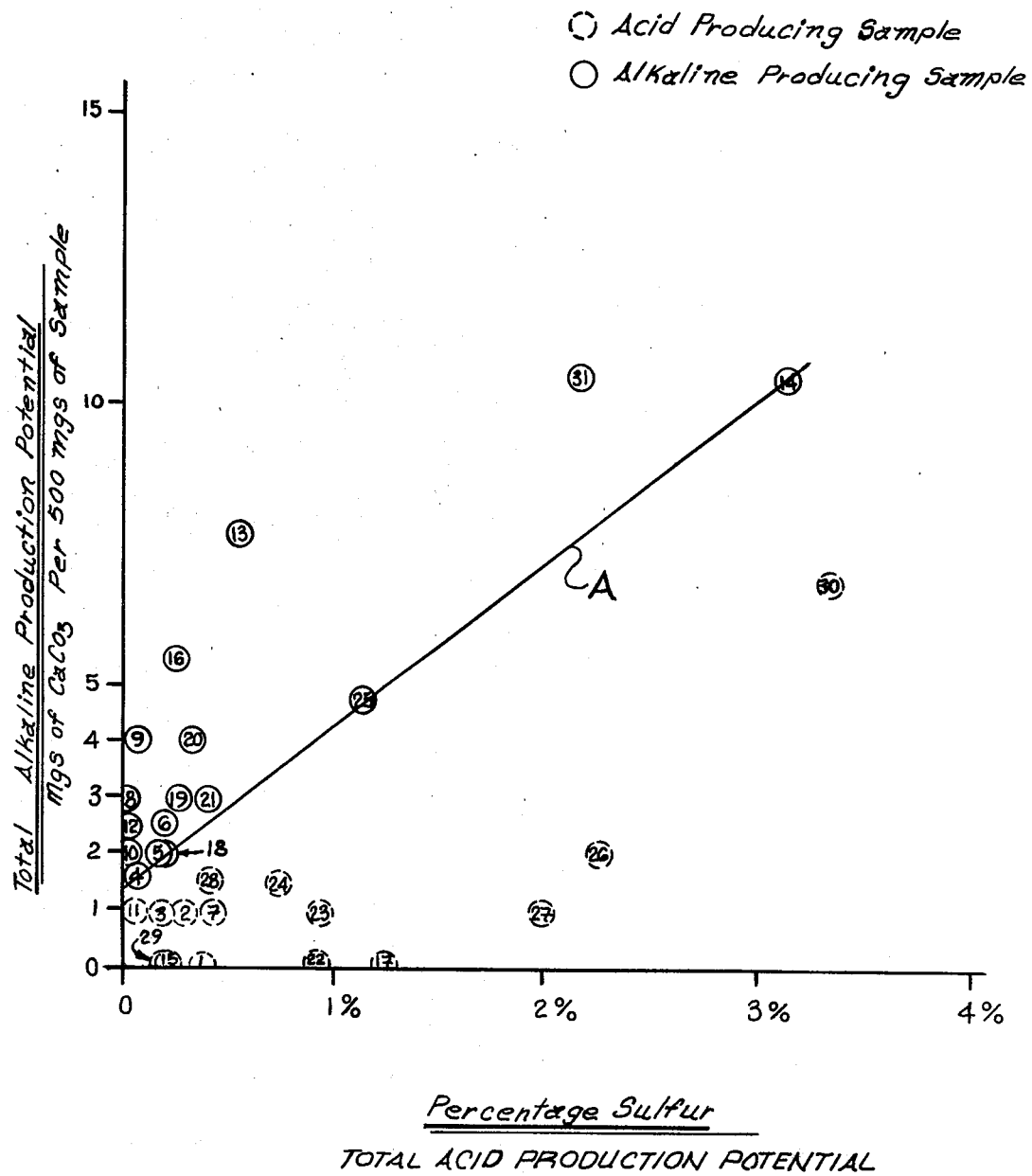

METHOD OF DETERMINING WEATHERING CHARACTERISTICS OF ROCK FORMATIONS IN EARTH MOVING OPERATIONS

This invention relates to a method for analyzing geological rock types found in selected geographical areas to predict their potential effect on the environment during exposure to weathering conditions. More particularly, the invention relates to an improved method for more accurately predicting the potential acidity of water drainage from rock formations which may be subjected to natural weathering conditions during earth moving operations, such as in strip mining. The method produces technical information which may be presented in the form of a series of graphs, tables or mathematical equations each defining a boundary, or line, separating areas of expected acidity from expected alkalinity of water drainage from specific rock types found in a particular geographic area under weathering conditions. Such boundary information is thereafter used by a field operator for quickly and accurately assessing the anticipated chemical weathering attributes of subsequent similar rock types taken from the geographic area, to permit proper relocation of such materials in backfilling operations to minimize acid water drainage from the relocated materials and enhance surface mine reclamation efforts.

BACKGROUND OF THE INVENTION

During earth moving operations, such as in the strip mining of coal, large volumes of rock overlying the coal seam (the overburden) are removed to expose the seam. This land perturbation can impact the environment with mine discharges that are laden with suspended sediment, dissolved solids, heavy and minor metals and elements and, in certain cases, acidic water drainages. Within a particular strip mine, numerous strata of varying mineralogies are disrupted by the mining process and the quality of drainage emanating from the mine site is a blend of water chemistries produced by each rock type.

Acid mine drainage is an extremely acidic, iron sulfate rich drainage that forms under natural conditions when certain coal seams are mined. The acidity in such mine drainage water is produced by oxidation of certain sulphur compounds occurring in the overlying strata which are exposed to the atmosphere. Sulphur is coal and the overburden can occur as organic sulphur, pyritic sulphur or sulphate sulphur. Organic sulphur is that component which is organically bound within the organic matter of the strata and is generally not chemically reactive under weathering conditions. Sulphate sulphur usually represents the water-soluble weathering products of the disulfides, and in most cases constitutes a very small percentage of the total sulphur content that is measured in a geologic section. Pyritic sulphur is that sulphur which is found in the disulfide phase, usually as either marcasite or pyrite.

Iron sulfides, occurring primarily as marcasite or pyrite in the coal and overlying strata, which become exposed to the atmosphere and oxidize in the presence of humidity and oxygen, form soluble hydrous iron sulfates. Subsequent natural water movement dissolves these compounds which hydrolyze to produce highly acidic water drainages with high concentrations of iron and sulfate.

Chemical reactions explaining the oxidation of the iron disulfide and the generation of acidity are given by the following equations:

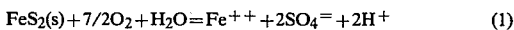

$$FeS_2(s) + 7/2 O_2 + H_2O = Fe^{++} + 2SO_4^= + 2H^+ \qquad (1)$$

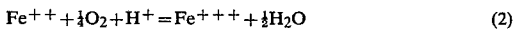

$$Fe^{++} + \tfrac{1}{4}O_2 + H^+ = Fe^{+++} + \tfrac{1}{2}H_2O \qquad (2)$$

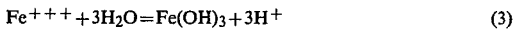

$$Fe^{+++} + 3H_2O = Fe(OH)_3 + 3H^+ \qquad (3)$$

The ferrous iron generated in the reaction described in equation (1) can be further oxidized to the ferric state in accordance with equation (3) and generate additional amounts of acidity. The ferric hydroxides associated with the chemical reaction in equation (3) impart the red and yellow-orange color that is characteristic of acid mine water drainage. Such acid drainage can greatly impact and undesirably alter the natural environment and alter the ecological balance of the surrounding areas in which earth moving operations are conducted.

Calcium and magnesium carbonate (calcareous) materials appearing in various rock types also have a dominating influence on rock weathering characteristics. However, unlike the acid-forming reactions, the geochemistry of alkaline production from calcareous material is constrained by the low solubility of the calcareous minerals in water. As a result, water in contact with calcareous materials produces alkalinity concentrations that are fixed by the partial pressure of carbon dioxide ($pCO_2$), the time of water contact, and the solubility constant of the specific mineral or rock, e.g., calcite, dolomite, limestone. This relationship, using calcite as the mineral, is expressed by the following equation:

$$\log Ca^{++}(\text{mg/liter}) = 2.56 + 0.362 \log pCO_2$$

and for every mole of calcium produced there are two moles of bicarbonate ($HCO_3^-$) alkalinity. Under natural conditions, the concentration of alkalinity of various rocks exposed to weathering conditions determines the level of acidity that can be absorbed and neutralized by the water system before it degrades to acid conditions. However, since the geochemistry of alkaline production is constrained by the low solubility of the calcareous material in water, the alkalinity concentrations produced in waters in contact with the calcareous materials vary with the time of contact and the aforementioned solubility constants of the specific materials with the waters.

Recent federal legislation enacted in connection with mining operations requires the submission of certain environmental resources information, including hydrological and geological data, for the permitting of mining operations. Included within such federal rules and regulations is a required submission of chemical analysis of the strata within the overburden of the proposed mine plan areas. Samples are usually taken from test borings and core samples, and are used to identify, at a minimum, those rock types which contain potential acid forming, or alkalinity producing materials. Federal regulations further require submission of a description of probable hydrological consequences of the proposed mining activities under expected seasonal conditions in the mining area, to predict the acid-forming characteristics of the water drainage from the area. Backfilled materials are required to be placed so as to minimize contamination of ground water systems with acid or otherwise harmful mine drainage, and to control or prevent discharge of acid, toxic or otherwise harmful mine drainage waters into adjacent water systems.

Thus, in the protection of the ecology of areas of land perturbation, the identification of potentially alkaline and acid producing strata is of central concern in mine permitting, mine planning and operation, and mine reclamation. With the capability of such identification, cores of overburden rock can be examined and the weathering characteristics of the various rock types assessed before mining to ascertain the quality of mine drainage that can be expected from the mining operation. In addition, the occurrence and location of potentially acidic and alkaline materials in the overburden can be identified and selectively handled during day to day operation of the mine. Further, in the course of reclaiming a mine, strata identified as potentially acidic can be relocated in lowermost layers of the replaced overburden so as to reduce their potential for creating acid water drainage.

Within the past decade, a variety of techniques have been developed which attempt to either predict a rock's weathering behavior, or anticipate the total acid or alkaline load of a rock calculated from its calcareous or pyritic sulphur content. As aforementioned, under natural conditions, the rate of release of alkalinity and acidity varies to a great extent, such that extended periods of time (weeks to months) would be required to fully assess the exact chemical weathering attributes of a particular stratum under natural weathering conditions. It has been proposed to simulate the effects of weathering characteristics on exposed rock strata by an accelerated leaching technique wherein samples of rock types from an area of interest are placed in inert chambers and subjected to a continuous flow of humidified air. Periodically, each sample is flushed with an aqueous medium and the effluent analyzed for various components indicative of certain reactions. The components analyzed were the acitidy, pH, alkalinity, and calcium, magnesium and sulphate ion concentrations. By placing the sample in an oxidizing environment and periodically flushing the sample, the field conditions of normal atmospheric oxidation of the samples with occasional flushings by rainfall may be simulated. Such a technique is described in our previously published articles entitled "Geochemical Factors Affecting Coal Mine Drainage Quality," Chapter 8, pages 129–148 of *Reclamation of Drastically Disturbed Lands,* 1978 By ASA-CSSA-SSSA, Madison, Wis.; and "Time As A Factor in Acid Mine Drainage Pollution," pages 41–50 of *Papers Presented Before The Seventh Symposium on Coal Mine Drainage Research,* NCA/BCR Coal Conference and Expo IV October 18-20, 1977 in Louisville, Kentucky, published by and obtainable from Bituminous Coal Research, Inc., Monroeville, Pennsylvania.

Such simulated weathering condition technique still requires an extended period of time in which to carry out the leaching operation to obtain the necessary data, and considerable laboratory equipment not readily available at mine site locations is required. Thus, such leaching techniques are not practical for field operation use to assess the weathering behavior of rock types at the mine site and their projected impact on mine drainage quality.

Certain prior art techniques have attempted to accelerate sulfide oxidation by the use of either strong oxidants, such as peroxide, or iron-catalyzing bacteria, to measure the amount of acidity that can be expected. Although such information may be useful in certain mining situations involving high grade igneous and metamorphic sulfide deposits, wherein the expected acid concentrations can be used for lime treatment requirements of the waste material and serve as a guide for treatment scheduling, the accelerated technique neglects the dimension of alkalinity and its neutralizing effect on ultimate acid mine drainage characteristics; therefore, such technique is generally unreliable in the assessment of the sedimentary rocks in coal mining regions.

Another prior art technique that purportedly evaluates the acid/base account of various overburden materials to predict the type of drainage that may be expected to occur with time, involves the steps of chemically digesting a pulverized portion of a rock sample to measure its pyritic sulphur content. Such sulphur content is then stoichiometrically related by equations (1)–(3), above, to the total amount of acidity that the rock can produce. Another portion of the same sample is digested in a hot hydrochloric acid solution and the amount of acid neutralized by the sample is determined by back titration with a standard base. This acid uptake is related to the total amount of alkalinity that the rock can produce. Balancing the "acid" and "base" totals determines whether an excess of acid or base exists, and supposedly predicts the chemical weathering attributes of the rock sample. However, because of the natural carbonate solubility constraint, as aforementioned, coupled with a partial pressure of carbon dioxide, an equilibrium condition is established which fixes the maximum amount of alkalinity that can be derived from calcareous material, whereas, conversely, the sulfide weathering product has almost infinite solubility. As a result, the kinetics of acid formation are radically different from those of alkalinity formation, and a serious error can be made when the rock's capacity to directly produce acidity or alkalinity is related, on a one to one basis, to the predicted concentrations which may occur within an aqueous drainage system.

In terms of predicting a rock's chemical weathering attribute, a similar error is made in the above technique in balancing the acid-base account of a particular rock unit. This fundamental error, which occurs because of the difference in kinetics of the acidity alkalinity formation, makes the technique unreliable for predicting chemical weathering attributes of various rock types. In addition, hot acid digestion of a rock breaks down the clay minerals and dissolves all siderite (iron carbonate, which will produce acid if the iron released oxidizes from the ferrous to the ferric state) and appears as part of the "base" account in the analysis. Since these components of the rock do not produce alkalinity under natural conditions, the technique is misleading when it measures them as alkaline producers.

Thus, a major problem which still exists in overburden analysis (as to whether rock will produce acidity, alkalinity or remain inert), centers about the ability to perform rapid and accurate determinations of parameters that predict long term weathering characteristics of rocks.

OBJECTS OF THE PRESENT INVENTION

Thus, it is an object of the present invention to provide a more accurate analytical method of assessing the anticipated chemical weathering attributes of commonly occurring rocks in a particular geographic area of interest than heretofore employed in the prior art.

It is another object to provide a method of analysis and resulting technical information which will quickly and efficiently accommodate the needs of various personnel associated with a mining program on the planning, permitting and regulatory levels.

It is a further object to provide a method of rock analysis under simulated weathering conditions in a particular geographic area of common geological characteristics, to produce graphic or mathematical boundary information separating and defining areas or zones of potential acidity and alkalinity of mine water drainage from easily identifiable rock types, which boundary information may be subsequently employed in on-site locations by mine personnel in combination with rapidly performable, on site analysis to more accurately predict the weathering attributes of the various rock types.

BRIEF DESCRIPTION OF THE INVENTION

Basically, the present invention involves the method steps of obtaining representative rock samples from a selected geographical area of consideration; visually classifying the rock samples as to basic rock type by their physical characteristics and reference to standard petrology texts, subjecting a representative portion of each rock sample to a humidified environment over an abbreviated period of time to simulate the longer term natural weathering conditions of the samples in the geographic area; periodically leaching the samples during the time period in which they are subjected to the humidified environment; analyzing the leachates obtained from each sample over such period of time to determine their net acidity or alkalinity; directly chemically analyzing another portion of each sample to determine its total acidity and alkalinity potential; and thereafter interrelating the total acidity potential to the total alkalinity potential of each rock sample of each rock type while identifying each interrelation as acid or alkaline by its corresponding leachate value, to define a boundary between areas or zones of expected acidity or alkalinity. The resultant information, which preferably may be presented in the form of graphs of defined acid and alkaline areas for each rock type, may thereafter be employed at various locations within the geographic and geological area of consideration, in combination with rapid direct chemical analysis techniques on selected rock samples, to more accurately and rapidly predict their weathering attributes as to acidity or alkalinity.

In contrast to prior art techniques which attempt to infer drainage quality only from bulk rock chemistry analysis, the present method incorporates the empirical results obtained in simulated weathering conditions on the representative rock types in a geographic area of consideration in combination with direct chemical techniques, which subsequently may be performed in the field, to obtain more reliable and accurate predictions of rock weathering characteristics than heretofore possible.

BRIEF DESCRIPTION OF THE DRAWINGS

The invention will be better understood from the following detailed description of preferred embodiments of the invention, when taken together with the accompanying FIGURE of the drawing which depicts a graph of interrelated acid and alkaline total production potential and leachate values of samples of a particular rock type from which boundary information, in a form of a line or curve, is derived.

DETAILED DESCRIPTION OF PREFERRED EMBODIMENTS

Based upon our discovery and recognition that the chemical weathering attributes of different rock types as to acidity or alkalinity was not directly predictable from the total acid or alkaline characteristics of the rocks as determined by direct chemical digestion procedures, (due to the difference of kinetics of release and water solubility of pyritic and calcareous materials in the rocks), we have developed a method utilizing chemical weathering attributes of different rock types in an area of interest, in combination with two easily measured parameters obtained by direct chemical analysis of the rock samples, to constructing a series of graphs depicting boundary and acid and alkaline arae information thereon. Two rapid chemical analysis parameters of subsequent rock samples of like type can then be plotted on the previously constructed boundary graph for that rock type to fall within the delineated areas or zones on the graph of acidity and alkalinity to give immediate indication of the chemical nature and weathering attributes of the rock samples.

As aforementioned, whether a rock from a particular mining region produces an acid or alkaline leachate, or drainage, depends upon the proportion of iron sulfide (FeS-FeS$_2$) and calcareous material (Ca,Mg—CO$_3$) present within the sample. Obviously, the presence of alkaline material in the absence of acid-producing materials will produce alkaline leachates, or water drainage, and vice versa. The situation, however, becomes more complex when a rock sample contains both alkaline and acid producing material in various proportions. The exact chemical interaction of these components is even more unpredictable from direct chemical analysis due to the variability and the kinetics of release of the acid and alkaline species into the water drainage from the various mineralogies.

Therefore, the present method relates the chemical weathering attributes of each of the different rock types found in a geographic area to two easily measured chemical analysis parameters of such rocks. The weathering characteristic graph for each rock type is constructed by first procuring a number of samples representative of commonly occurring rocks or minerals indigenous to a geographic area of interest and identifying the different samples as to basic rock type. Rock types can be visually identified and classified, in well known manner, by their several physical characteristics, e.g., mineralogy, grain size and texture, with subsequent reference to a classification scheme found in a standard textbook of petrology. Many texts are available for this purpose, such as *Guide to the Study of Rocks* by L. E. Spock, 1953, Harper and Brothers, Publishers, New York and *Physical Geology Laboratory Manual*, by Hamblin and Howard, 1971, Burgess Publishing Co., Minneapolis, Minn.

Although numerous rock types exist, within a given geographic region, only a few rock types usually predominate. Therefore, for a particular geographic area of study, the geology can be generalized and the number of different rock types reduced to a characteristic few.

A portion of numerous samples of each identified rock type is then chemically analyzed for the percentages of total alkaline and acid producing components in each sample, i.e., the total acid and alkaline production potential of the sample. A further portion of each sample is also subjected to simulated weathering conditions and the net acidity or alkalinity of each leachate is determined by standard pH and titration procedures as described in *Standard Methods for the Examination of Water and Wastewater*, 13th Edition, American Public Health Assoc., Washington, D.C., 20036. A leachate with an initial pH of less than 4.5 has no alkalinity, is defined as having a net acidity, and is titrated to an end point of 8.3. A leachate with an initial pH that is greater than 8.3 has no acidity, is defined as having net alkalinity, and is titrated to an end point of 4.5. Those samples which produce leachates with pH values between 4.5 and 8.3 are titrated to both end points to obtain their acidity and alkalinity concentrations. The difference between these concentrations defines the samples as having either net acidity or net alkalinity, depending upon the excess of one component over the other.

The net acidity or alkalinity is determined for each leaching interval. An overall net acidity or alkalinity value is calculated for the duration of the leaching tests by differentiation of the concentration values, i.e., by the addition of all net acidities and alkalinities (derived from each leaching interval) to determine which of the two components is in excess at the conclusion of the leaching tests.

The total acid and alkaline producing components of the rock sample (expressed as percentages and milligrams of $CaCO_3$ per 500 mg. of sample, respectively,) are then interrelated, as by graphically plotting the two against each other, and the resulting plots are labeled as acid or alkaline from the weathering leachate data to define areas that are delineated as acid and alkaline within the chemical matrix plot. Once a boundary between these areas is established, unknown rock samples may thereafter be measured for the two total content parameters which are plotted on the boundary graph to fall within a particular area of anticipated weathering response. This forms the basis for the more accurate prediction of weathering characteristics of rock samples by the simple two parameter data system.

The following specific example illustrates the manner in which the method of the present invention may be carried out to construct a graphic representation of boundary information which may be subsequently utilized by a field worker in a particular geographical area of interest to rapidly and more accurately predict the weathering characteristics of various rock formations occurring in the area. Although the specific example given herein illustrates the acid/alkaline area information in the form of a boundary graph of the areas, it can be understood that the boundary information of acid and alkaline areas or zones for each rock type may be provided in the form of a mathematical equation, table, or computerized program, which a field worker may utilize to predict weathering characteristics of other rock samples by the simplified two-step direct analysis procedure.

EXAMPLE 1

A number of rock samples were collected from a water shed area in southwestern Pennsylvania. The particular area selected was proposed for coal strip mining operations. Continuous cores of rock overlying a coal seam were bored from selected ground locations in the overburden area of the seam with the use of a diamond tip core barrel of a rotary drill. The layers of rock units occurring in each core boring were selectively segregated, as to rock type, on the basis of visual identification of their physical characteristics, and by reference to a standard textbook of petrology. In the area studied, seven distinctive rock groups were identified: sandstone, limestone, shale, calcareous shale, coal, binder and seat earth. The shales had the greatest frequency of occurrence and only this rock type is used to form a boundary graph in accordance with the following example. Obviously boundary graphs of the other predominant rock types in the geographic area will be produced in like manner as that described for the shales.

Representative portions of each rock type occurring in the cores obtained from the overburden were collected, packaged and transported to a chemical testing laboratory.

Each rock sample collected was crushed with a jaw crusher to pass a four millimeter sieve, and each crushed sample was then split by conventional cone and quartering procedure into one large and two smaller representative sample portions. The larger portion of each rock sample was subjected to simulated weathering conditions that approximated those expected to occur naturally in the area of interest. One of the smaller portions was used to determine the mineralogic components of the rock that might produce acidity, alkalinity, and the other smaller portion was set aside for direct chemical analysis for acid and alkaline production potential. The following analytical procedures were employed.

The smaller portion of each rock sample employed for mineralogic identification (15–20 grams) was ground further by a rock grinder to pass a two millimeter sieve, air dried, and a representative portion thereof withdrawn and cast into a one inch diameter Buehler plastic mold using APCO epoxy. The pellets were cured for 24 hours and polished by Buehler polishing wheels until the surface of the pellet was suitable for reflected light microscope examination. Utilizing standard reflected light microscopy techniques, the mineralogical constituents of each sample were examined. Pyrite was identified as the major acid producing mineral and calcium carbonate was identified as the primary alkaline producing mineral in the samples.

To ascertain the predicted weathering characteristics of the rock samples obtained, the larger portions of each rock sample were air dried, weighed and placed in separate covered plastic chambers. A continuous flow of humidified air was passed over each sample for an extended period of time of approximately thirty days. At selected intervals of three to six days, the samples were covered with 100 milliliters of deionized water, stirred, and the leachate generated therefrom decanted into 100 milliliter beakers. Two aliquots of each leachate were withdrawn with a pipet, each transferred to a 50 milliliter beaker and the pH measured. If the pH was greater than 8.3, the sample was analyzed only for alkalinity and determined to have a net alkalinity equal to the measured value. If the pH was less than 4.5, the sample was analyzed only for acidity and determined to have a net acidity equal to the measured value. If the sample pH was between 4.5 and 8.3, the sample was analyzed for both acidity and alkalinity. The difference between these two values and the excess of one over the other determined whether the sample had a net acidity or net alkalinity. All analyses were done in accordance with standard potentiometric titration techniques described in *Standard Methods For The Examination of Water And Waste Water*, 13th Edition, published jointly by American Public Health, Assoc., American Water Works Assoc. and Water Pollution Control Federation.

More specifically an aliquot portion of each leachate was measured for cold pH and another for hot pH. Hot pH refers to the pH of a sample that was boiled for two minutes and allowed to cool to room temperature. If the cold pH was less than 8.3 and the hot pH was greater than 4.5, the boiled sample was titrated with a standard alkali solution to an endpoint of pH 8.3 to quantitatively measure the amount of acidity present. The other unboiled aliquot was titrated with a standard acid solution to an endpoint of pH 4.5 to quantitatively measure the amount of alkalinity present. The difference between the two values is the net acidity or alkalinity. If, as mentioned previously, the initial cold pH was greater than 8.3, then the sample had a net alkalinity, alternatively, if the hot pH was less than 4.5, then the sample had a net acidity. Standard conversion factors were employed to convert the number of milliliters of titrant required to bring the samples to the endpoints, to obtain acidity or alkalinity values expressed as equivalent milligrams of calcium carbonate ($CaCO_3$).

The alkalinity and/or acidity values obtained from each sample (expressed in milligrams of $CaCO_3$) were subtracted to obtain a net alkalinity of acidity value. This value was used to characterize the leachate of each rock sample as to whether the sample produces alkaline or acidic drainage therefrom under natural weathering conditions for a period of approximately 30 days. The results of these net acidity or alkalinity values for the shale rock samples are shown in Table 1.

TABLE 1

Summary of Leachate Quality and Total Acid and Alkaline Production Potential

| Sample No. | Leachate Analysis | First Leaching | Second Leaching | Third Leaching | Fourth Leaching | Fifth Leaching | Sixth Leaching | Seventh Leaching | Weathering Attribute | Sulfur Content | Alkaline Production Potential mg of $CaCO_3$ per 500 mgs |
|---|---|---|---|---|---|---|---|---|---|---|---|
| 1 | Acidity | 0.41 | 1.10 | 0.83 | 0.89 | 1.23 | 1.52 | | | | |
|   | Alkalinity | 0 | 0 | 0 | 0 | 0 | 0 | | | | |
|   | Net | 0.41 | 1.10 | 0.83 | 0.89 | 1.23 | 1.52 | | Acid | 0.37% | 0 |
| 2 | Acidity | 0.77 | 0.98 | 0.78 | 0.25 | 0.19 | 0.17 | | | | |
|   | Alkalinity | 0 | 0 | 0 | 0 | 0.08 | 0.10 | | | | |
|   | Net | 0.77 | 0.98 | 0.78 | 0.25 | 0.11 | 0.07 | | Acid | 0.34% | 1 |
| 3 | Acidity | 0.09 | 0.19 | 0.23 | 0.27 | 0.27 | 0.26 | | | | |
|   | Alkalinity | * | 0.04 | 0.03 | 0.03 | 0.03 | 0.07 | | | | |
|   | Net | | 0.15 | 0.20 | 0.24 | 0.24 | 0.19 | | Acid | 0.21% | 1 |
| 4 | Acidity | 0.24 | 0.08 | 0.07 | 0.07 | 0.07 | 0.09 | | | | |
|   | Alkalinity | * | 0.11 | 0.14 | 0.14 | 0.21 | 0.20 | | | | |
|   | Net | | 0.03 | 0.07 | 0.07 | 0.14 | 0.11 | | Alkaline | 0.16% | 1.6 |
| 5 | Acidity | 0.15 | 0.10 | 0.05 | 0.07 | 0.11 | 0.08 | | | | |
|   | Alkalinity | * | 0.18 | 0.27 | 0.34 | 0.43 | 0.53 | | | | |
|   | Net | | 0.08 | 0.22 | 0.27 | 0.32 | 0.45 | | Alkaline | 0.21% | 2 |
| 6 | Acidity | 0.12 | 0.07 | 0.08 | 0.09 | 0.13 | 0.09 | | | | |
|   | Alkalinity | * | 0.14 | 0.15 | 0.15 | 0.22 | 0.20 | | | | |
|   | Net | | 0.07 | 0.07 | 0.06 | 0.09 | 0.11 | | Alkaline | 0.21% | 2.6 |
| 7 | Acidity | 0.21 | 0.32 | 0.39 | 0.15 | 0.13 | 0.05 | 0.58 | | | |
|   | Alkalinity | 0 | * | 0.07 | 0.07 | 0.01 | 0.11 | 0.12 | | | |
|   | Net | 0.21 | | 0.32 | 0.08 | 0.12 | 0.06 | 0.46 | Acid | 0.49% | 1 |
| 8 | Acidity | 0.10 | 0.10 | 0 | 0 | 0.10 | 0 | 0 | | | |
|   | Alkalinity | 0.91 | 0.68 | 0.53 | 0.63 | 0.55 | 1.10 | 0.53 | | | |
|   | Net | 0.81 | 0.58 | 0.53 | 0.63 | 0.45 | 1.10 | 0.53 | Alkaline | 0.01% | 3 |
| 9 | Acidity | 0 | 0 | 0 | 0 | 0 | 0 | 0 | | | |
|   | Alkalinity | 0.39 | 1.18 | 1.27 | 1.23 | 1.24 | 1.08 | 1.28 | | | |
|   | Net | 0.39 | 1.18 | 1.27 | 1.23 | 1.24 | 1.08 | 1.28 | Alkaline | 0.11% | 4 |
| 10 | Acidity | 0 | 0 | 0 | 0 | 0 | 0 | 0 | | | |
|   | Alkalinity | 0.29 | 1.36 | 1.75 | 1.34 | 1.97 | 1.77 | 1.58 | | | |
|   | Net | 0.29 | 1.36 | 1.75 | 1.34 | 1.97 | 1.77 | 1.58 | Alkaline | 0 | 2 |
| 11 | Acidity | 0.18 | 0.28 | 0.17 | 0.21 | 0.4 | 0.53 | 0.36 | | | |
|   | Alkalinity | 0 | 0 | 0.06 | 0 | 0 | 0 | 0 | | | |
|   | Net | 0.18 | 0.28 | 0.11 | 0.21 | 0.4 | 0.53 | 0.36 | Acid | 0.12% | 1 |
| 12 | Acidity | 0.11 | 0.09 | 0.0 | 0.0 | 0.0 | 0.0 | 0.0 | | | |
|   | Alkalinity | 0.10 | 0.45 | 0.56 | 0.60 | 0.85 | 0.73 | 0.77 | | | |
|   | Net | 0.01 | 0.36 | 0.56 | 0.60 | 0.85 | 0.73 | 0.77 | Alkaline | 0.01% | 2.5 |
| 13 | Acidity | * | 0.08 | 0.0 | 0.09 | 0.0 | 0.0 | 0.0 | | | |
|   | Alkalinity | 0.51 | 0.77 | 0.67 | 0.74 | 0.84 | 0.97 | 1.15 | | | |
|   | Net | | 0.69 | 0.67 | 0.65 | 0.84 | 0.97 | 1.15 | Alkaline | 0.63% | 7.5 |
| 14 | Acidity | 0 | 0 | 0 | 0 | 0 | 0 | 0 | | | |
|   | Alkalinity | 0.87 | 0.79 | 0.78 | 0.72 | 0.78 | 0.76 | 0.65 | | | |
|   | Net | 0.87 | 0.79 | 0.78 | 0.72 | 0.78 | 0.76 | 0.65 | Alkaline | 3.15% | 11.5 |
| 15 | Acidity | 1.43 | 1.15 | 0.83 | 0.64 | 0.67 | 0.57 | 0.64 | | | |
|   | Alkalinity | 0 | 0 | 0 | 0 | 0 | 0 | 0 | | | |
|   | Net | 1.43 | 1.15 | 0.83 | 0.64 | 0.67 | 0.57 | 0.64 | Acid | 0.2% | 0 |
| 16 | Acidity | 0.11 | 0.09 | 0.09 | 0.38 | 0.15 | 0.09 | 0.18 | | | |
|   | Alkalinity | * | 0.19 | 0.22 | 0.23 | 0.27 | 0.26 | 0.18 | | | |
|   | Net | | 0.19 | 0.13 | 0.15 | 0.12 | 0.17 | 0 | Alkaline | 0.26% | 5.5 |
| 17 | Acidity | 17.68 | 42.02 | 30.1 | 17.9 | 19.04 | 12.29 | 26.48 | | | |
|   | Alkalinity | 0 | 0 | 0 | 0 | 0 | 0 | 0 | | | |
|   | Net | 17.68 | 42.02 | 30.1 | 17.9 | 19.04 | 12.29 | 26.48 | Acid | 1.37% | 0 |
| 18 | Acidity | 0.10 | 0.0 | 0 | 0 | 0 | 0 | | | | |
|   | Alkalinity | 0.59 | 0.70 | 0.87 | 0.79 | 0.77 | 0.75 | | | | |
|   | Net | 0.49 | 0.70 | 0.87 | 0.79 | 0.77 | 0.75 | | Alkaline | 0.22% | 2 |
| 19 | Acidity | 0 | 0 | 0 | 0 | 0 | 0 | | | | |
|   | Alkalinity | 0.43 | 0.62 | 0.86 | 0.58 | 0.46 | 0.42 | | | | |

TABLE 1-continued

Summary of Leachate Quality and Total Acid and Alkaline Production Potential

| Sample No. | Leachate Analysis | First Leaching | Second Leaching | Third Leaching | Fourth Leaching | Fifth Leaching | Sixth Leaching | Seventh Leaching | Weathering Attribute | Sulfur Content | Alkaline Production Potential mg of $CaCO_3$ per 500 mgs |
|---|---|---|---|---|---|---|---|---|---|---|---|
|  | Net | 0.43 | 0.62 | 0.86 | 0.58 | 0.46 | 0.42 |  | Alkaline | 0.25% | 3 |
| 20 | Acidity | 0.14 | 0.13 | 0.09 | 0.07 | 0.11 | 0.07 |  |  |  |  |
|  | Alkalinity | * | 0.26 | 0.23 | 0.21 | 0.31 | 0.22 |  |  |  |  |
|  | Net |  | 0.13 | 0.14 | 0.14 | 0.20 | 0.15 |  | Alkaline | 0.31% | 4 |
| 21 | Acidity | 0.08 | 0.07 | 0.06 | 0.09 | 0.08 | 0.07 |  |  |  |  |
|  | Alkalinity | * | 0.19 | 0.32 | 0.27 | 0.32 | 0.22 |  |  |  |  |
|  | Net | 0.87 | 0.12 | 0.26 | 0.18 | 0.24 | 0.15 |  | Alkaline | 0.44% | 3 |
| 22 | Acidity | 3.29 | 1.68 | 1.86 | 0.97 | 1.13 | 1.15 | 2.02 |  |  |  |
|  | Alkalinity | 0 | 0 | 0 | 0 | 0 | 0 | 0 |  |  |  |
|  | Net | 3.29 | 1.68 | 1.86 | 0.97 | 0 | 1.15 | 2.02 | Acid | 0.95% | 0 |
| 23 | Acidity | 3.34 | 1.63 | 3.71 | 2.38 | 6.36 | 5.23 | 11.76 |  |  |  |
|  | Alkalinity | 0 | 0 | 0 | 0 | 0 | 0 | 0 |  |  |  |
|  | Net | 3.34 | 1.63 | 3.71 | 2.38 | 6.36 | 5.23 | 11.76 | Acid | 0.96% | 1 |
| 24 | Acidity | 2.02 | 0.98 | 1.13 | 0.95 | 1.64 | 1.35 | 2.01 |  |  |  |
|  | Alkalinity | 0 | 0 | 0 | 0 | 0 | 0 | 0 |  |  |  |
|  | Net | 2.02 | 0.98 | 1.13 | 0.95 | 1.64 | 1.35 | 2.01 | Acid | 0.77% | 1.6 |
| 25 | Acidity | 0 | 0 | 0 | 0 | 0 | 0 | 0 |  |  |  |
|  | Alkalinity | 1.0 | 1.1 | 1.7 | 1.2 | 1.1 | 1.6 | 1.5 |  |  |  |
|  | Net | 1.0 | 1.1 | 1.7 | 1.2 | 1.1 | 1.6 | 1.5 | Alkaline | 1.16% | 4.8 |
| 26 | Acidity | 4.15 | 0.63 | 0.92 | 1.48 | 2.48 | 3.38 | 4.63 |  |  |  |
|  | Alkalinity | 0 | 0 | 0 | 0 | 0 | 0 | 0 |  |  |  |
|  | Net | 4.15 | 0.63 | 0.92 | 1.48 | 2.48 | 3.38 | 4.63 | Acid | 2.33% | 2 |
| 27 | Acidity | 6.43 | 10.10 | 4.23 | 2.57 | 2.93 | 2.63 | 2.64 |  |  |  |
|  | Alkalinity | 0 | 0 | 0 | 0 | 0 | 0 | 0 |  |  |  |
|  | Net | 6.43 | 10.10 | 4.23 | 2.57 | 2.93 | 2.63 | 2.64 | Acid | 2.0% | 1 |
| 28 | Acidity | 1.20 | 2.53 | 2.05 | 1.89 | 3.26 | 5.19 | 4.94 |  |  |  |
|  | Alkalinity | 0 | 0 | 0 | 0 | 0 | 0 | 0 |  |  |  |
|  | Net | 1.20 | 2.53 | 2.05 | 1.89 | 3.26 | 5.19 | 4.94 | Acid | 0.46% | 1.5 |
| 29 | Acidity | 0.19 | 0.26 | 0.28 | 0.36 | 0.36 | 0.38 | 0.50 |  |  |  |
|  | Alkalinity | 0 | 0 | 0 | 0 | 0 | 0 | 0 |  |  |  |
|  | Net | 0.19 | 0.26 | 0.28 | 0.36 | 0.36 | 0.38 | 0.50 | Acid | 0.19% | 0 |
| 30 | Acidity | 114 | 156 | 121 | 101 | 74.2 |  |  |  |  |  |
|  | Alkalinity | 0 | 0 | 0 | 0 | 0 |  |  |  |  |  |
|  | Net | 114 | 156 | 121 | 101 | 74.2 |  |  | Acid | 3.36% | 6.8 |
| 31 | Acidity | 0 | 0 | 0 | 0 | 0 | 0 | 0 |  |  |  |
|  | Alkalinity | 0.89 | 1.42 | 1.58 | 1.10 | 1.17 | 1.37 | 0.71 |  |  |  |
|  | Net | 0.89 | 1.42 | 1.58 | 1.10 | 1.17 | 1.37 | 0.71 | Alkaline | 2.2% | 10.5 |

*Insufficient leachate precluded running both analyses

The third portion of each rock sample used for direct chemical analysis was further ground by a rock grinder to pass a two millimeter sieve, pulverized to pass a 100 micron sieve, air dried and stored in glass bottles. Two precisely weighed samples were withdrawn from the bottles by rolling the bottle to rotate the sample and removing 5 to 10 mg (milligram) increments until a 50.0 mg portion was removed. This was placed in a ceramic crucible for total sulfur analysis. Similarly, a 500.0 mg portion was removed and placed in a 100 ml beaker for alkaline production potential analysis.

Because pyrite was identified as the major acid producer, the measure of the sulfur content of the sample would reflect the total acid production potential of the sample. An alternative method would be to measure the pyritic iron content of the sample. If some other sulfide mineral had been identified as the major acid producer, the cation associated with that mineral would be measured. The total sulfur content of the samples was measured with a LECO (Laboratory Equipment Company) induction furnace and automatic titrator. Total sulfur analyses can also be performed by the Eschka and Bomb Washing methods given in ASTM Methods for Coal and Coke Analysis, pp. 674–677: Section D 3177-73.

The remaining 500.0 mg sample was analyzed for its total alkaline production potential by a cold acid digestion technique in which 25 mls of 0.10 N hydrochloric acid solution were added to the sample in the beaker, the solution stirred with a glass rod and the beaker covered with a watch glass. The sample was digested at room temperature (20° C.) for 2.5 hours with frequent stirring. Following digestion, the solution was titrated with 0.10 N sodium hydroxide to an endpoint of 4.5 which was potentiometrically determined. The calcium carbonate equivalents of the alkaline production potential was determined from a standard curve prepared by digesting known weights of reagent grade calcium carbonate by the same procedure and plotting the amount of calcium carbonate digested versus the milliliters of 0.10 N sodium hydroxide required to bring the sample to the predetermined end point of 4.5.

If the pH of the pulverized rock sample-acid solution was 4.5 or greater after the digestion period, a second portion of the sample was analyzed by weighing out another 500.0 mg portion, placing it in a beaker and adding 50 mls of 0.10 N hydrochloric acid; instead of 25 mls of acid solution. The sample was similarly digested and titrated to an endpoint of pH 4.5 and a new curve was generated with calcium carbonate standards digested with 50 mls of acid in a manner similar to the one described above.

The results obtained by these two direct chemical analyses, in addition to the results of the leaching tests, are shown in Table 1. From these data, the graph of the drawing was developed. The total sulfur content, as a measure of the total acid production potential was plotted on the absissa and the total alkaline production potential, expressed as mgs of calcium carbonate per 500 mgs of sample was plotted on the ordinate. The acid and alkaline production potentials of each sample were then plotted and labeled as acid or alkaline, as indicated on the graph, based on the results of the weathering leachate data. Each of the shale rock samples is marked by a number which corresponds to the numbered point shown in the graph comprising the FIGURE of the drawing. This served to define areas where samples were delineated as having the potential to produce acid or alkaline leachates. The two areas were separated by the boundary line A. From this boundary-lined graph, the potential of new samples to produce acid or alkaline leachates can be assessed by noting the total sulfur content and alkaline production potential analysis of the new sample, and plotting the same against each other to fall in the area above or below the boundary line A.

As can be seen from the graph of the FIGURE, the plotted total acid alkaline potential points of each sample which have been correspondingly identified as acid or alkaline by their leachate, simulated weathering characteristics, lie in distinct separate areas of the graph, and the boundary line A separating the two areas is located to fall closely adjacent to or along the lowermost alkaline-identified points of the graph. Since the acid producing shale rock samples are of primary concern as an environmental hazard in mine permitting, planning and rock handling operations, the boundary line A has been located more closely to the alkaline plots as a safety factor to ensure that no potentially acid producing rock sample plot lying adjacent the boundary area will be incorrectly identified as alkaline producing. Obviously, more precise location of the boundary line separating the alkaline and acid areas of the graph can be achieved by further sampling of shale rock types in the geographic location of interest to obtain more graphic plots falling closely adjacent the boundary between the areas.

The foregoing specific example of the method of preparing a boundary graph defining acid and alkaline weathering characteristic areas for the shale rock types, would of course be repeated with the other identified rock types in the area to produce a corresponding boundary graph for each of such rock types. These boundary graphs, along with standard visual rock type identification information, such as the standard text materials identified hereinabove, are supplied to on site personnel to enable the personnel to rapidly and more accurately predict the weathering characteristics of the rock formations by the described direct chemical analysis of total acid production and alkaline production procedures which may be readily performed at the on site locations.

From the foregoing, it can be seen that the improved methods of analysis of the present invention produce technical data information in the form of graphs, charts, mathematical equations or computer program information which may be employed to rapidly and more accurately predict weathering characteristics of rock types prior to and during earth moving operations.

That which is claimed is:

1. A method for predicting the potential acidity or alkalinity of water drainage from rock formations which may be subjected to natural weathering conditions during earth moving operations, comprising the steps of:

(a) obtaining a plurality of representative rock samples from a selected geographic area of interest;

(b) classifying each sample as to rock type;

(c) subjecting a portion of each rock sample to an environment to permit its oxidation for a predetermined period of time, while periodically leaching the sample portion with an aqueous medium during said period and collecting the leachates obtained therefrom;

(d) chemically analyzing each leachate obtained from each rock sample during said period to determine the net acidity or alkalinity of the leachates from the sample;

(e) subjecting further portions of each characterized rock sample to direct chemical analysis to quantitatively determine its total acidity production potential and its total alkalinity production potential;

(f) interrelating the quantitative results of the total acidity production potential and the total alkalinity production potential of each rock sample of the classified type;

(g) identifying each rock sample interrelation as acidic or alkaline as established by its corresponding leachate net acidity or alkalinity to establish resultant boundary information defining separate areas of acidity interrelations and alkalinity interrelations; and thereafter (h) classifying additional rock samples from the geographic areas as to rock type, directly chemically analyzing each of the additional samples of each rock type to quantitatively determine its total acidity production potential and its total alkalinity production potential; interrelating the quantitative results of each additional rock sample's total acid production potential and total alkalinity production potential with the boundary information for its particular rock type to identify the same as in said area of acidity or said area of alkalinity, whereby the potential acidity or alkalinity of water drainage from each sample of the type under natural weathering conditions is predicted.

2. A method as defined in claim 1 wherein the quantitative results of the total acidity production potential and the total alkalinity production potential of each rock sample of the classified type is interrelated by graphically plotting the quantitative results of the total acidity production potential against the total alkalinity production potential of each rock sample of the type; and said resultant boundary information is established by identifying each rock sample type plot as acidic or alkaline as established by its corresponding leachate characterization, and separating sample plots identified as alkaline from sample plots identified as acid by visual indicia on the graph to define said separate areas of acidity and alkalinity.

3. A method as defined in claim 2 wherein quantitative results of each additional rock sample's total acid production potential and its total alkalinity production potential is interrelated with said boundary information by plotting the quantitative total acid production potential of each additional sample against its quantitative total alkaline production potential on said graph to fall within said defined areas of acidity or alkalinity.

4. A method as defined in claim 2 wherein the net leachate acidity or alkalinity concentration level of each rock sample is determined by titrating the leachates with standard acid and base solutions to selected end points, and the quantitative titration acidity and alkalinity equivalents are differentiated to determine the net leachate acidity or alkalinity of the rock sample.

5. A method as defined in claim 4 wherein each leachate acidity or alkalinity equivalent is determined, respectively, by titration of the leachate to end points of 4.5 and 8.3 pH.

6. A method as defined in claim 1 wherein the total acidity production potential of each rock sample is quantitatively determined by determining the total percentage of sulfur present in the sample, and wherein the total alkalinity production potential of each rock sample is determined by cold digestion of a portion of the sample in a standard acid followed by back titration of the digested sample portion with a standard base.

7. A method as defined in claim 1 wherein a portion of each rock sample is subjected to a humidified environment to permit its oxidation for said predetermined period of time, and is leached with distilled water at periodic intervals during said period to produce said leachates.

8. A method as defined in claim 1 wherein each sample is classified as to rock type by comparison of its physical appearance with standard visual representations of rock samples of varying type.

9. A method for producing graphic or mathematical boundary information for use in predicting the potential acidity or alkalinity of water drainage from rock types in a geographic area, which rock types may be subject to natural weathering conditions, comprising the steps of:
(a) subjecting a plurality of rock samples of common type taken from a geographic area of interest to simulated weathering conditions by oxidizing a portion of each of the samples for a predetermined period of time,
(b) periodically leaching the sample portions during said period of time with an aqueous medium,
(c) chemically analyzing the leachates of each sample portion to determine the net acidity or alkalinity of the leachate,
(d) subjecting further portions of each rock sample to direct chemical analysis to quantitatively determine the total acidity production potential and the total alkalinity production potential of the sample,
(e) interrelating the quantitative results of total acidity production potential of each sample with its total alkalinity production potential to generate graphic or mathematical information,
(f) identifying each rock sample interrelation as acidic or alkaline as determined by its corresponding net leachate acidity or alkalinity and recording the same with said graphic or mathematical information to produce resultant boundary information defining separate areas of acidity interrelations and alkalinity interrelations, whereby said boundary information may be employed with quantitative total acidity and alkalinity production potential values of subsequent rock samples of like type obtained in the geographic area to predict the potential acidity or alkalinity of water drainage therefrom under natural weathering conditions.

10. A method as defined in claim 9 wherein the quantitative results of total acidity production potential and total alkalinity production potential of each sample is interrelated by graphically plotting the quantitative results of the total acidity production potential against the total alkalinity production potential of each rock sample of the type; and said resultant boundary information is produced by identifying each rock sample type plotted as acidic or alkaline as established by its corresponding leachate net acidity or alkalinity, and separating sample plots identified as alkaline from sample plots identified as acid on the graph to define said separate areas of acidity and alkalinity.

11. A method as defined in claim 10 wherein the net acidity or alkalinity of the leachates of each rock sample of the type is determined by titrating each leachate of the rock sample with standard acid and base solutions to respective pH end points of 4.5 and 8.3 to obtain their acidity and alkalinity concentration, and differentiating the acidity and alkalinity concentrations to establish a net leachate acidity or alkalinity for the rock sample.

12. A method as defined in claim 11 wherein the total acidity production potential of each rock sample is quantitatively determined by determining the total percentage of sulfur present in the sample, and wherein the total alkalinity production potential of each rock sample is determined by cold digestion of a portion of the sample in a standard acid followed by back titration of the digested sample portion with a standard base.

13. A method as defined in claim 9 wherein a portion of each rock sample is subjected to a humidified environment to permit its oxidation for said predetermined period of time, and said sample is leached with distilled water at periodic intervals during said period of time to produce said leachates.

14. A boundary information product produced by the method of claim 9.

15. A graph product produced by the method of claim 10.

* * * * *

UNITED STATES PATENT AND TRADEMARK OFFICE
CERTIFICATE OF CORRECTION

PATENT NO. : 4,328,001
DATED : May 4, 1982
INVENTOR(S) : Frank T. Caruccio and Gwendelyn G. Caruccio It is certified that error appears in the above-identified patent and that said Letters Patent are hereby corrected as shown below:

Column 1, line 49, "is" should read --in--.

Column 10, line 9, "of" should read --or--.

Column 14, claim 1,(h), line 27, "areas" should read -- area--.

Signed and Sealed this

Twenty-ninth Day of June 1982

[SEAL]

Attest:

GERALD J. MOSSINGHOFF

Attesting Officer     Commissioner of Patents and Trademarks